US006616652B1

(12) United States Patent
Harper et al.

(10) Patent No.: US 6,616,652 B1
(45) Date of Patent: Sep. 9, 2003

(54) OSMOTIC PUMP DELIVERY SYSTEM WITH PRE-HYDRATED MEMBRANE(S) AND/OR PRIMABLE CATHETER

(75) Inventors: Derek J. Harper, Santa Barbara, CA (US); Charles F. Milo, Atherton, CA (US)

(73) Assignee: Microsolutions, Inc., Goleta, CA (US)

( * ) Notice: Subject to any disclaimer, the term of this patent is extended or adjusted under 35 U.S.C. 154(b) by 0 days.

(21) Appl. No.: 09/504,603

(22) Filed: Feb. 15, 2000

(51) Int. Cl.$^7$ ................................................. A61K 9/22
(52) U.S. Cl. .................................................... 604/892.1
(58) Field of Search ......................... 604/890.1, 891.1, 604/892.1, 288, 93.01; 424/422–424

(56) References Cited

U.S. PATENT DOCUMENTS

| 3,760,984 A | | 9/1973 | Theeuwes |
| 3,845,770 A | | 11/1974 | Theeuwes |
| 3,916,899 A | | 11/1975 | Theeuwes |
| 3,977,404 A | | 8/1976 | Theeuwes |
| 3,987,790 A | | 10/1976 | Eckenhoff et al. |
| 4,587,117 A | | 5/1986 | Edgren |
| 4,723,958 A | | 2/1988 | Pope |
| 4,783,413 A | | 11/1988 | Suter |
| 4,838,862 A | * | 6/1989 | Baker et al. ................. 604/244 |
| 5,257,987 A | * | 11/1993 | Athayde et al. ....... 128/DIG. 12 |
| 5,312,389 A | * | 5/1994 | Theeuwes et al. ........... 222/389 |
| 5,607,696 A | | 3/1997 | Rivera et al. |
| 5,672,167 A | * | 9/1997 | Athayde et al. ............. 604/131 |
| 5,728,396 A | | 3/1998 | Peery et al. |
| 5,801,188 A | | 9/1998 | Hassenbusch |
| 5,807,328 A | * | 9/1998 | Briscoe .................. 604/102.02 |
| 5,869,096 A | | 2/1999 | Barclay |
| 5,869,097 A | | 2/1999 | Wong |
| 5,876,752 A | | 3/1999 | Herbig |
| 5,904,934 A | | 5/1999 | Maruyama |
| 5,919,160 A | * | 7/1999 | Sanfilippo, II ............... 604/19 |
| 5,980,509 A | | 11/1999 | Magruder |
| 5,985,305 A | | 11/1999 | Peery |

FOREIGN PATENT DOCUMENTS

WO  WO 00/54745  3/1999

OTHER PUBLICATIONS

Jon P. Monk, Rosemary Beresford and Alan Ward, *Sufentanil: A Review Of Its Pharmacological And therapeutic Use*, Drugs 36, pp. 268–313, 1988.

(List continued on next page.)

*Primary Examiner*—Brian L. Casler
*Assistant Examiner*—Matthew DeSanto
(74) *Attorney, Agent, or Firm*—Young Law Firm, P.C.

(57) ABSTRACT

An implantable osmotic pump system includes a prehydrated semipermeable membrane to reduce the time interval between implantation of the system into the patient and full operation of the pump system. The semipermeable membrane is maintained in a hydrated state prior to implantation by fluid contact with a saline solution maintained in a saturated state by a salt tablet. As the differential osmotic pressure across the hydrated semipermeable membrane is negligible as the saline concentration on both sides of the membrane is the same, the pump system does not operate and does not infuse the pharmaceutical agent as long as this osmotic equipotential state is maintained. When the saturated saline solution is removed from fluid contact with the semipermeable membrane and the system is implanted in a patient, the osmotic pressure differential across the semipermeable membrane increases, thereby causing the pump to immediately begin operation at or near its intended and designed steady state infusion rate. To further decrease the delay between implantation and effusion of a pharmaceutical agent from the system, the infusion lumen of an attached catheter may be at least partially flushed with the same or a different pharmaceutical agent as is loaded in the pharmaceutical agent compartment of the pump system.

35 Claims, 3 Drawing Sheets

OTHER PUBLICATIONS

F.P. Boerma, M.D.; H. Noorduin, M.SC. and G. Vanden Bussche, M.D., *Epidural Sufentanil For Cancer Pain Control In Outpatients*, Regional Anestehesia, November–December vol. 14, No. 6, pp. 293–297, 1989.

Tim J. Lamer, M.D.; Symposium on Pain Management—Part II, *Treatment Of Cancer–Related Pain: When Orally Administered Medications Fail*, Mayo Clinic Proc., 69, pp. 473–480, 1994.

T.F. Meert and M. DeKock, *Potentiation Of The Analgesic Properties Of Fentanyl–Like Opioids With Alpha2–Adrenoceptor Agonists In Rats*, Anesthesiology, September, 81(3), pp. 677–688, 1994.

A. Paix, A. Coleman, J. Lees, J. Grigson, M. Brooksbank, D. Thorne and M. Ashby, *Subcutaneous Fentanyl And Sufentanil Infusion Substitution For Morphine Intolerance In Cancer Pain Management*, Pain, November; 63(2), pp. 263–269, 1995.

F. Mercier, M. Dounas, H. Bouaziz, V. Des Mesnard–Smaja, C. Foiret, M.N. Vestermann, M. Fischler and D. Benhamou, *The Effect Of Adding A Minidose Of Clonidine To Intrathecal Sufentanil For Labor Analgesia*, Anesthesiology, September 89(3), pp. 594–601, 1998.

Alzet Osmotic Pumps, *References from 1991–1998 On The Administration Of Opiods Using ALZET Osmotic Pumps (OPIQ–Q4–99)*, pp. 1–13, World Wide Web, http://www.alzet.com/bibliography/bib_pages/opio.htm (Printed on Oct. 13, 2000).

* cited by examiner

OSMOTIC PUMP DELIVERY SYSTEM WITH PRE-HYDRATED MEMBRANE(S) AND/OR PRIMABLE CATHETER

CROSS-REFERENCE TO RELATED APPLICATIONS

This application is related in subject matter to commonly assigned patent application Ser. No. 09/442,128 filed on Nov. 16, 1999 entitled "Methods And Implantable Devices And Systems For Long Term Delivery Of A Pharmaceutical Agent", the disclosure of which is hereby incorporated herein in its entirety.

This application is also related in subject matter to commonly assigned patent application Ser. No. 09/503,821 filed on Feb. 15, 2000 and entitled "Osmotic Pump Delivery System With Flexible Drug Compartment", the disclosure of which is also hereby incorporated herein in its entirety.

This application is also related in subject matter to commonly assigned patent application Ser. No. 09/504,971 filed on Feb. 15, 2000 and entitled "Osmotic Pump Delivery System With Flexible Drug Compartment", the disclosure of which is also hereby incorporated herein in its entirety.

BACKGROUND OF THE INVENTION

1. Field of the Invention

The present invention relates generally to the field of drug delivery systems. In particular, the present invention relates to osmotic pump systems, devices, kits and associated methods for shortening the time interval between implantation of the osmotic pump system and delivery of a pharmaceutical agent to the patient.

2. Description of the Related Art

Since the beginning of modern medicine, drugs have been administered orally. Patients have taken pills as recommended by their physician. The pills must pass through the digestive system and then the liver before they reach their intended delivery site (e.g., the vascular system). The actions of the digestive tract and the liver often reduce the efficacy of medication; furthermore, medications delivered systemically sometimes cause undesirable side effects. Over the course of the past few decades, drug delivery technology and administration has evolved from oral delivery to site-specific delivery. In addition to the oral route of administration, drugs are also routinely administered via the vascular system (intravenous or IV). Intravenous drug delivery has the advantage of bypassing the acidic and enzymatic action of the digestive system. Unfortunately, IV administration requires the use of a percutaneous catheter or needle to deliver the drug to the vein. The percutaneous site requires extra cleanliness and maintenance to minimize the risk of infection. Infection is such a significant risk that IV administration is often limited to a number of weeks, at most. In addition, the patient must wear an external pump connected to the percutaneous catheter.

The next step in the evolution of drug delivery was the implanted pump. The implanted pump is a device that is completely implanted under the skin of a patient, thereby negating the need for a percutaneous catheter. These implanted pumps provide the patient with a drug at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump. Fully implanted constant rate and programmable rate infusion pumps have been sold in the United States for human use since the late 1970s and early 1980s, respectively. Two problems associated with such 1970s and 1980s vintage constant rate and programmable rate infusion pumps relate to their size and their cost. Current implantable constant rate and programmable pumps are about the size and shape of hockey pucks, and they typically are sold to the hospital for $5,000–$9,000. The current implantable pumps must be implanted in the Operating Room under general anesthesia, which further increases costs, as well as the risk, and discomfort to the patient. The size and cost of such pumps has proven to be a substantial barrier to their use, and they are rarely used to deliver medication. An added drawback of phase-change and peristaltic pumps is that they must be refilled with drug every 3–8 weeks. Refills constitute an added burden to the caregiver, and add further costs to an already overburdened healthcare system. The burden associated with such refills, therefore, further limits the use of phase-change and peristaltic pumps.

In the 1970s, a new approach toward implanted pump design was commercialized for animal use only. The driving force of the pumps based upon this new approach utilized the principle of osmosis. Osmotic pumps may be much smaller than other constant rate or programmable pumps, because their infusion rate can be very low. A recent example of such a pump is described listed in U.S. Pat. No. 5,728,396. This patent discloses an implantable osmotic pump that achieves a sustained delivery of leuprolide. The pump includes an impermeable reservoir that.is divided into a water-swellable agent chamber and a drug chamber. Fluid from the body is imbibed through a semi permeable plug into the water-swellable agent chamber and the drug is released through a diffusion outlet at a substantially constant rate.

Once implanted, however, conventional osmotic pump systems do not begin infusing drug into the patient immediately. Indeed, the semi permeable plug, initially dry before implantation, must first become thoroughly hydrated with the patient's bodily fluids after implantation before the pump will deliver the drug at the intended and designed infusion rate. This time interval between implantation and full hydration of the semi permeable plug is non-trivial, and is usually on the order of several hours to 2–4 days. In the case wherein the pump contains pain medication, this means that the patient must endure a long delay before the pump begins to work as designed (i.e., at its steady state infusion rate) and.provides the expected relief. Often, therefore, the surgeon must provide the patient with additional medication to bridge the gap between implantation of the osmotic pump system and full operation thereof. Patients, therefore, would be well served with osmotic pump delivery systems that would begin infusing drug at the intended rate immediately or soon after implantation.

Further adding to this delay is the catheter attached to the osmotic pump. The catheter is designed to carry the drug from the osmotic pump to the intended delivery site within the patient, whether a subcutaneous, epidural, subdural, subarachnoid, intravenous or intraventricular location, for example. The infusion lumen of the catheter defines an internal volume called the dead volume of the catheter. Upon first implantation of a osmotic pump system, the drug pushed out of the pump's drug compartment must flow the entire length of the catheter before reaching the intended delivery site. The time required for the drug to do so further adds to the already long hydration delay and further delays any benefit to be derived from using an implantable pump system. Patients would also be well served, therefore, with methods, devices and systems to shorten or eliminate the delay in delivery of the drug attributable to the dead volume of the catheter.

A conventional osmotic pump system, however, does start to infuse some amount of drug as the semi permeable plug hydrates. However, the amount of drug that is infused as the plug hydrates is often unknown and unpredictable. Indeed, the rate at which the plug hydrates may vary upon many factors, such as the composition and thickness of the semi permeable plug, as well as the hydration levels of the implantation site of the system within the patient. Therefore, it becomes difficult for the surgeon to estimate the effective drug delivery rate in the first few hours and days after implantation. This may render the surgeon overly conservative or unduly aggressive when administering pain medication to bridge the aforementioned gap between initial implantation and full hydration of the semi permeable plug. Indeed, the surgeon may administer less (or more) drug than the therapeutically optimal amount. This is because the surgeon has no way of reliably estimating the current amount of drug being infused into the patient soon after implantation of the osmotic device, as the semi permeable plug thereof typically does not hydrate at a constant or predictable rate in all situations.

There is believed to have been a long felt need for osmotic pump systems, devices and associated methods in which the initial delivery rate of pharmaceutical agent is predictable, and occurs at substantially the designed steady state infusion rate.

SUMMARY OF THE INVENTION

It is an object of the present invention, therefore, to provide osmotic pump delivery systems that begin infusing a pharmaceutical agent at the intended rate immediately or soon after implantation. It is a further object of the present invention to provide methods, devices and systems to shorten or eliminate the delay in delivery of the drug caused by the dead volume of the catheter. It is a still further object of the present invention to provide osmotic pump systems, devices and associated methods in which the initial delivery rate of pharmaceutical agent is predictable, and occurs at substantially the intended steady state rate.

In accordance with the above-described objects and those that will be mentioned and will become apparent below, a kit, according to an embodiment of the present invention, comprises a liquid tight container enclosing an implantable osmotic pump, the pump including a semipermeable membrane; a salt tablet, and a saturated saline solution, the saline solution being in fluid contact at least with the salt tablet and the semipermeable membrane.

According to further embodiments, a catheter may be attached to the osmotic pump. The catheter may include a distal valve mechanism adapted to prevent fluid back flow into the catheter. The saturated saline solution may be in fluid contact with the osmotic pump and the tablet. The container may be or may include a flexible fluid-tight bag made of or including, for example, polyethylene, PET, PETG and/or a gas permeable barrier film. The osmotic pump may be preloaded with a pharmaceutical agent. For example, the osmotic pump may be preloaded with one or more pharmaceutical agents for pain therapy, hormone therapy, gene therapy, angiogenic therapy, anti-tumor therapy, chemotherapy and/or other pharmaceutical therapies. In the case of pain therapy, the pharmaceutical agent pre-loaded into the pump system may include one or more of the drugs fentanyl, sufentanil and clonidine, and mixtures thereof. The catheter may include a flushing valve near a proximal end thereof. The catheter may be formed of an elastomeric, polymeric or composite materials such as silicone or polyurethane and the flushing valve may is include or be formed as a longitudinal slit in the catheter. The kit may further include an ampoule containing a pharmaceutical agent therein, and a syringe fitted with an extension tube, a distal end of which is dimensioned to fit within the proximal flushing valve of the catheter.

The present invention may also be seen as a method of packaging an implantable osmotic pump system, the system including an implantable osmotic pump including a semipermeable membrane at one end and a catheter fitted to another end thereof, comprising the steps of disposing the osmotic pump in a liquid tight container; disposing a salt tablet within the container; at least partially filling the container with a saline solution such that the solution is in fluid contact at least with the semipermeable membrane and the salt tablet, and sealing the container. A step of sterilizing the sealed container may also be carried out. The disposing, filling and sealing steps may also be carried out aseptically.

Alternatively, the present invention may be viewed as a method of shortening a time from implantation of an osmotic pump system to delivery of a first pharmaceutical agent to a patient, the osmotic pump system including a semipermeable membrane at one end and a catheter including an infusion lumen at another end thereof, the method comprising the steps of pre-hydrating the semipermeable membrane prior to implantation of the pump system into the patient; flushing a dead volume of the infusion lumen with a second pharmaceutical agent, and implanting the osmotic pump system.

According to further embodiments, the pre-hydrating step may include the step of packaging the osmotic pump system in a liquid tight container including a saline solution. The packaging step may include a step of placing a salt tablet in the saline solution to maintain the solution in a saturated state. Alternatively, the osmotic pump system may include an impermeable membrane covering the semipermeable membrane and defining an interstitial hydration compartment therewith, the hydration compartment containing a saturated saline solution therein and the method may further comprise the step of breaching the impermeable membrane prior to the implanting step. The catheter may include a proximal flushing valve, and the flushing step may include the step of injecting the pharmaceutical agent into the infusion lumen through the proximal flushing valve. The injecting step may include the steps of drawing a sufficient amount of the pharmaceutical agent to fill the dead volume of the infusion lumen into a syringe fitted with an extension tube, disposing a free end of the extension tube into the proximal flushing valve, depressing a plunger of the syringe and removing the extension tube from the proximal flushing valve.

The present invention is also an implantable osmotic pump system, comprising a pump housing having a proximal and a distal end, the pump housing including a pharmaceutical agent compartment and an osmotic agent compartment separated by a movable piston; a semipermeable membrane fitted to the proximal end; an impermeable membrane disposed over and away from the semipermeable membrane to define a fluid tight hydration compartment therewith and a saturated saline solution within the hydration compartment.

According to further embodiments, a salt tablet may be disposed in the hydration compartment. The impermeable barrier may include titanium, stainless steel, platinum, platinum-iridium, PET and/or PETG, for example. The impermeable membrane may be configured to be breached with a lancet prior to implantation of the osmotic pump system in a patient. The pharmaceutical agent compartment may be preloaded with a pharmaceutical agent. For example, the pharmaceutical agent may include one or more of the following drugs: fentanyl, sufentanil and clonidine. The osmotic pump system may be preloaded with one or more pharmaceutical agents for pain therapy, hormone therapy, gene therapy, angiogenic therapy, anti-tumor therapy, chemotherapy and/or other pharmaceutical therapies. A catheter may be attached to the distal end of the pump housing, the attached catheter being in fluid communication with the pharmaceutical agent compartment. The catheter may include an infusion lumen and an elastomeric proximal flushing valve. The catheter may include a distal valve mechanism adapted to prevent fluid back flow into the catheter.

The present invention is also a kit comprising an implantable osmotic pump system, comprising a pump housing having a proximal and a distal end, the pump housing including a pharmaceutical agent compartment and an osmotic agent compartment separated by a movable piston; a semipermeable membrane fitted to the proximal end; an impermeable membrane disposed over and away from the semipermeable membrane to define a fluid tight hydration compartment therewith and a saturated saline solution within the hydration compartment, and a lancet adapted to breach the impermeable barrier.

A salt tablet may be disposed in the hydration compartment. The impermeable barrier may include titanium and/or stainless steel, platinum, platinum-iridium, PET and/or PETG, for example. The impermeable membrane may be configured to be breached with a lancet prior to implantation of the osmotic pump system in a patient. The pharmaceutical agent compartment may be preloaded with a pharmaceutical agent. The pharmaceutical agent may include fentanyl, sufentanil and/or clonidine. The osmotic pump system may be preloaded with one or more pharmaceutical agents for pain therapy, hormone therapy, gene therapy, angiogenic therapy, anti-tumor therapy, chemotherapy and/or other pharmaceutical therapies. A catheter may be attached to the distal end of the pump housing and in fluid communication with the pharmaceutical agent compartment. The catheter may include an infusion lumen and an elastomeric proximal flushing valve. The catheter may include a distal valve mechanism adapted to prevent fluid back flow into the catheter. A syringe adapted to inject pharmaceutical agent into the infusion lumen through the proximal valve may also be included in the kit. The syringe may include an extension tube fitted thereto, the free end thereof being adapted to fit into the proximal flushing valve. An ampoule may be included in the kit, the ampoule containing a sufficient volume of pharmaceutical agent to flush the infusion lumen prior to implantation of the osmotic pump system.

The present invention may also be viewed as a method of shortening a time interval between implantation of a pump system and first delivery of a pharmaceutical agent to the patient, the pump system including a pump housing having a proximal end and a distal end, the distal end having a catheter attached thereto, the catheter including an infusion lumen defining a dead volume, the method comprising the steps of at least partially filling the dead volume of the infusion lumen with the pharmaceutical agent prior to implantation of the pump system into the patient, and implanting the pump system into the patient.

The pump system may be an osmotic pump system including a semi permeable membrane fitted to the proximal end of the pump housing and wherein the method further comprises the step of pre-hydrating the semi permeable membrane prior to the implanting step. The pre-hydrating step may pre-hydrate the semi permeable membrane with a saturated saline solution.

According to a still further embodiment of the present invention, a method of shortening a time from implantation of a pump system to first delivery of a first pharmaceutical agent to a patient, the pump system including a pump housing containing a first pharmaceutical agent and a catheter including an infusion lumen, comprises the steps of flushing a dead volume of the infusion lumen with a second pharmaceutical agent, and implanting the pump system.

The first and second pharmaceutical agents may be the same or different pharmaceutical agents. The catheter may include a proximal flushing valve, and the flushing step may include the step of injecting the second pharmaceutical agent into the infusion lumen through the proximal flushing valve. The injecting step may include the steps of drawing a sufficient amount of the second pharmaceutical agent to fill the dead volume of the infusion lumen into a syringe fitted with an extension tube, disposing a free end of the extension tube into the proximal flushing valve, depressing a plunger of the syringe and removing the extension tube from the proximal flushing valve.

BRIEF DESCRIPTION OF THE DRAWINGS

For a further understanding of the objects and advantages of the present invention, reference should be made to the following detailed description, taken in conjunction with the accompanying figures, in which.

Figure 3A:
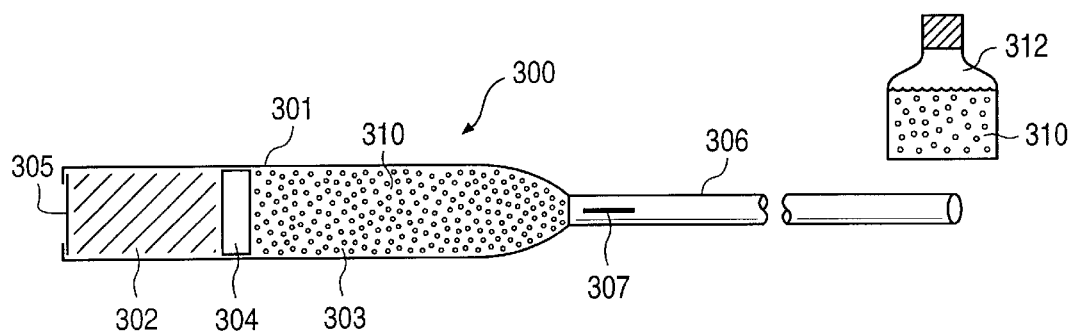
FIGS. 3a through 3c are schematic illustrations of a pharmaceutical agent delivery method, implantable pump system and kit, according to still further embodiments of the present invention.
Figure 3B:
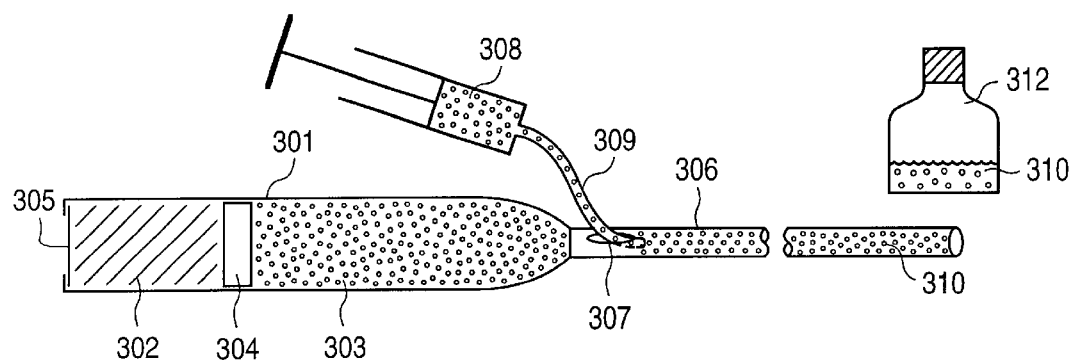
Figure 3C:
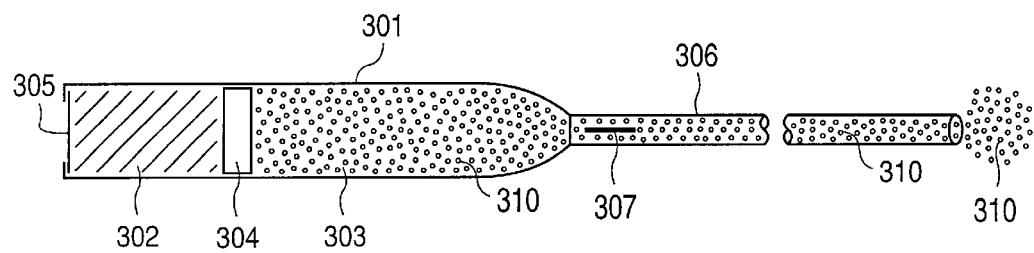

Specifically,

FIG. 3a is a schematic illustration of a pharmaceutical agent delivery device including a proximal flushing valve, prior to the surgeon flushing the catheter infusion lumen;

FIG. 3b is a schematic illustration of the delivery device of FIG. 3a as the surgeon flushes the infusion lumen of the catheter, preparatory to implanting the delivery device into the patient, and FIG. 3c is a schematic illustration of the delivery device of FIG. 3b, after the surgeon has flushed the catheter infusion lumen.

DESCRIPTION OF THE INVENTION

Figure 1:
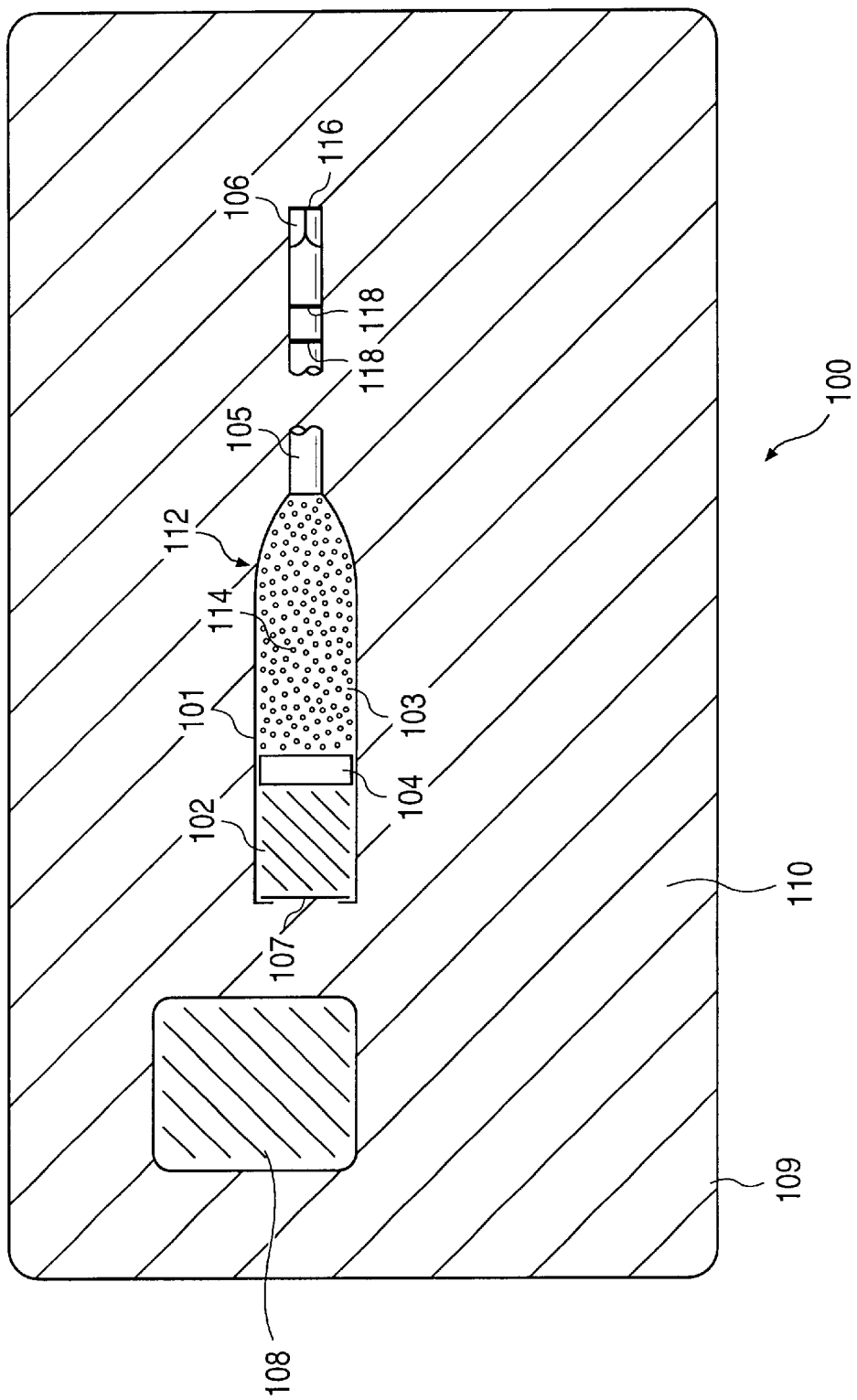
FIG. 1 is a schematic illustration of an implantable osmotic delivery system and kit according to an embodiment of the present invention.

FIG. 1 is a schematic illustration of an implantable osmotic delivery system and kit according to an embodiment of the present invention. As shown therein, an osmotic pump product 100 includes an osmotic pump system 112 packaged in a liquid tight container 109 containing a salt tablet 108 and a saline solution 110. The saline solution 110 is maintained in a saturated state by the salt tablet 108. The osmotic pump system 112, as shown in FIG. 1, includes a pump housing 101, which is divided into an osmotic engine compartment 102 and a pharmaceutical agent compartment 103 separated by a movable piston 104. The pharmaceutical agent compartment 103 may be pre-loaded with a volume of pharmaceutical agent 114. The pump housing 101 has a proximal end and a distal end. A semi permeable membrane 107 is fitted to the proximal end of the pump housing 101. The semi permeable membrane 107 may include, for example, cellulose acetate. A catheter 105 is connected to the distal end of the pump housing 101 and is in fluid communication with the pharmaceutical agent compartment 103 thereof.

According to the present invention, the saturated saline solution 110 is in fluid contact with at least the salt tablet 108 and the semi permeable membrane 107. According to a further embodiment of the present invention, the entire pump system 112 is immersed in the (sterile) saturated saline solution 110 upon packaging the pump system and prior to implantation of the system 112 into a patient. In this manner, the semi permeable membrane 107 in fully hydrated when the surgeon implants the pump system 112 into the patient, thereby eliminating or substantially shortening the time delay between implantation and first delivery of the pharmaceutical agent at the intended steady state delivery rate. Indeed, the osmotic pressure differential across the semipermeable membrane 107 is negligible while the osmotic pump system 112 is contained within the saline solution 110 that is maintained in a saturated state by the salt (NaCl, for example) tablet 108. As the osmotic pressure differential across the semi permeable membrane 107 is negligible, no or substantially no pharmaceutical agent 114 is pumped out of the pump housing 101, as long as this osmotic equipotential state is maintained across the semi permeable membrane 107. The saturated saline solution 110 also maintains the semi permeable membrane 107 is a fully hydrated state until the device is implanted into the patient. When the container 109 is opened and the osmotic pump system 112 is removed from the saturated saline solution 110 and implanted into the patient, the differential osmotic pressure across the semipermeable membrane 107 causes the material in the osmotic engine compartment 102 to enlarge in volume and push on the movable piston 104. This pushing of the movable piston 104 in the distal direction causes a corresponding decrease in the volume of the pharmaceutical agent compartment 103 and causes the pharmaceutical agent 114 contained therein to infuse through the infusion lumen of the catheter 105 to the intended delivery site at the distal most end of the catheter 105. The pump system 112 starts to function immediately at or near the intended (e.g., designed) steady state infusion rate because the semipermeable membrane 107 is pre-hydrated.

The catheter 105 may be formed of silicone or polyurethane, for example, and may be of a single or dual lumen design to accommodate a guidewire. A suitable dual lumen design is disclosed in commonly assigned U.S. patent application Ser. No. 09/442,128 entitled "Methods and Implantable devices And Systems For Long Term delivery Of A Pharmaceutical Agent" filed on Nov. 16, 1999, the disclosure of which is incorporated herewith in its entirety. The catheter 105 may terminate as an open lumen or may include a valve mechanism 106 as shown in FIG. 1. The valve 106 prevents back flow of the pharmaceutical agent released into the patient through the catheter infusion lumen and/or a guidewire lumen thereof. Such back flow may occur due to the pressure differential between the patient environment (such as the spinal fluid) and the free distal end of a catheter lumen. That is, the spinal fluid may be at a higher pressure than the pressure in the guidewire lumen and the outside. In the absence of a valve mechanism 106 or other means for preventing back flow, the pharmaceutical agent effluent and spinal fluid may tend to flow back proximally toward the pump housing 101 through guidewire lumen (once implanted). Such a distal valve 106 allows a guidewire to be pushed there through but prevents back flow of the pharmaceutical agent 114 or bodily fluids (such as spinal fluid) through the guidewire lumen of the catheter 105 when the guidewire is removed therefrom.

The distal end of the catheter 105, as shown in FIG. 1, may include a radiopaque marker 116 to allow the distal tip of the catheter 105 to be clearly visible through fluoroscopy. Such distal marker 116 facilitates the insertion of the catheter portion 105 of the implantable pump system 112 under fluoroscopic guidance in a radiology suite, for example. To further aid implantation of the pump system 112 under fluoroscopic guidance, radiopaque length markers 118 may be disposed on or incorporated within the length of the catheter 105. This allows the physician to gauge the length of catheter 105 inserted into the patient. Alternatively, the entire length of the catheter 105 may include a radiopaque material.

Alternatively still, the distal valve 106 may be relocated to the proximal (or near the proximal) end of the catheter and the distal radiopaque marker may be omitted in its entirety. Instead, the catheter 105 according to the present invention may be radiopaque over at least a portion of its entire length. The combination of a radiopaque catheter 105 and a proximally-located valve mechanism 106 allows the surgeon to adjust the length of the catheter 105 by trimming the distal end thereof according to the needs of the procedure at hand and/or the patient's anatomy. Any suitable radiopaque material may be used to render all or a portion or selected portions of the catheter 105 radiopaque. For example, the catheter 105 may be formed of silicone or polyurethane and may be doped with barium sulfate, for example. The length of the catheter 105 may be most any therapeutically effective length. A longer length, however, increases the catheter dead volume and delays the effusion of the pharmaceutical agent into the patient, as it will take longer for the agent to travel from the proximal.to the distal end of the catheter 105. For example, the catheter 105 may be about 5 cm to about 100 cm in length. More preferably, the catheter 105 may be about 10 cm to about 30 cm in length. More preferably still, the catheter 105 maybe about 15 cm to about 25 cm in length. For example, the catheter 105 may be about 20 cm in length. The internal diameter (ID) of the infusion lumen of the catheter 105 may be selected within the range of about 0.001 inches to about 0.010 inches. The walls of the catheter 105 may be about 0.001 inches to about 0.025 inches in thickness. According to an embodiment of the present invention, the outer diameter (OD) of the catheter 105 may be selected between about 0.024 inches and about 0.066 inches in thickness.

FIG. 1 may also be viewed as a kit including some or all of the constituent elements described above and/or a method of packaging an osmotic pump and/or pump system by enclosing the pump and/or pump system in a liquid-tight container at least partially filled with a saline solution, the saline solution being maintained in a saturated state by a salt tablet, as shown in FIG. 1 at reference numeral 108.

Figure 2A:
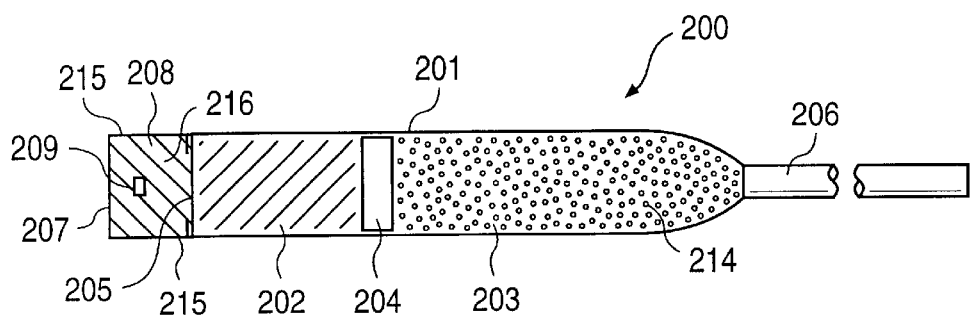
FIG. 2a is a schematic illustration of an implantable osmotic delivery system according to another embodiment of the present invention.

FIG. 2a is a schematic illustration of an implantable osmotic delivery system according to another embodiment of the present invention. As shown therein, the osmotic pump system 200 includes a pump housing 201 enclosing an osmotic engine compartment 202 and a pharmaceutical agent compartment 203 separated by a movable piston 204. The pharmaceutical agent compartment 203 may be pre-loaded with a volume of pharmaceutical agent 214. The pump housing 201 has a proximal end and a distal end. A semi permeable membrane 205 is fitted near the proximal end of the pump housing 201. The semi permeable membrane 205 may include, for example, cellulose acetate. A catheter 206 may be connected to the distal end of the pump housing 201 and may be in fluid communication with the pharmaceutical agent compartment 203 thereof.

According to this embodiment of the present invention, the osmotic pump system 200 includes an impermeable membrane 207 that covers the semipermeable membrane 205 and defines an interstitial hydration compartment 208 therewith, the hydration compartment 208 containing a saturated saline solution 216. To form the hydration compartment 208, the wall of the pump housing 201 may be extended past the semipermeable membrane 205 to form a spacer 215. The open end of the spacer 215 may then be covered with the impermeable membrane 207, which may then be welded thereon or otherwise attached thereto so as to form a fluid-tight hydration compartment 208 defined by the spacer 215, the semipermeable membrane 205 and the impermeable membrane 207. The impermeable membrane 207 may be formed, for example, of titanium and/or stainless steel, platinum, platinum-iridium, PET and/or PETG. Other means of forming the hydration compartment 208 will occur to those of skill in this art, and all such means should be deemed to fall within the scope of the present invention.

A small salt tablet 209 maintains the saline solution 216 within the hydration compartment 208 in a saturated state. The saturated saline solution 216 is in fluid contact with both the salt tablet 209 and the semipermeable membrane 205, thereby keeping the semipermeable membrane 205 in a fully hydrated state prior to implantation, with all of the advantages thereof described relative to the embodiments of FIG. 1. The saturated saline solution 216 in the hydration compartment 208 keeps the semipermeable membrane 205 hydrated during storage of the pump system 200. The osmotic pressure differential across the semipermeable membrane 205 is initially negligible, as the saline concentration is substantially the same on both sides of the semipermeable membrane 205. In the state shown in FIG. 2a, therefore, the pump system 200 does not function and does not infuse the pharmaceutical agent 214 through the catheter 206.

Figure 2B:
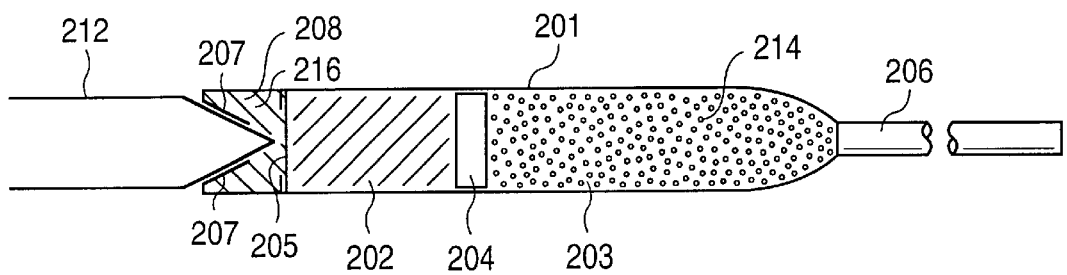
FIG. 2b is a schematic illustration of the implantable osmotic delivery system of FIG. 2a, as the impermeable membrane is breached by the surgeon.

Prior to implantation of the pump system 200, the impermeable membrane 207 is breached with a lancet 212, as shown in FIG. 2b. Preferably, the outer diameter of the lancet 212 is somewhat greater than the inner diameter of the spacer 215. These relative dimensions prevent the lancet 212 from being inadvertently inserted too far. That is, the relative dimensions of the lancet 212 and the spacer 215 are preferably such that when the lancet 212 breaches the impermeable membrane 207, the spacer 215 prevents the lancet 212 from damaging the underlying semi permeable membrane 205, breaching the osmotic driving compartment 202 or otherwise damaging the pump system 200. Preferably, the lancet 212 is inserted only as far as to breach the impermeable membrane 207 and to allow a free influx of water from the patient's body into the previously sealed hydration compartment 208 once the pump system 200 is implanted.

Figure 2C:
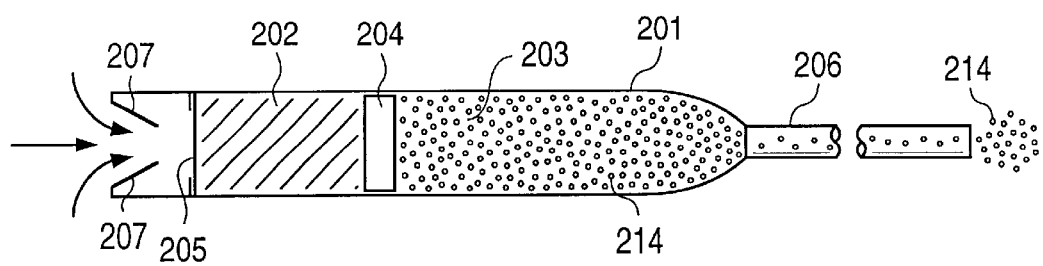
FIG. 2c is a schematic illustration of the system of FIG. 2b, after the surgeon has breached the impermeable membrane and implanted the system within the patient.

As shown in FIG. 2c, after the surgeon has breached the impermeable membrane 207 and implanted the pump system 200 in the patient, the increased differential osmotic pressure across the semipermeable membrane 205 causes the material in the osmotic engine compartment 202 to enlarge in volume and push on the movable piston 204, thereby decreasing the volume of the pharmaceutical agent compartment 203 and infusing the pharmaceutical agent 214 through the catheter 206 to the intended delivery site. The pump system 200 begins to function at or near the intended (e.g., designed) steady state infusion rate immediately or soon after implantation, as a result of the semipermeable membrane 205 being fully hydrated prior to implantation. The catheter 206 may include a distal or proximal valve mechanism 106, a distal radio-opaque marker 116 and/or radio-opaque length markers 118, as shown and described relative to FIG. 1. For brevity's sake, the description of these structures is incorporated herein as if repeated here in full.

FIGS. 3a through 3c are schematic illustrations of a pharmaceutical agent delivery method, implantable pump system and kit, according to still further embodiments of the present invention. FIG. 3a shows a pharmaceutical agent delivery device 300 including a pump housing 301 having the general structure of the pump housing of FIG. 1. Indeed, the pump housing includes an osmotic engine compartment 302 and a pharmaceutical agent compartment 303 separated by a movable piston 304. A semipermeable membrane 305 is fitted to the proximal end of the pump housing 301 and a catheter 306 is secured to the distal end thereof, in fluid communication with the pharmaceutical agent compartment 303. The catheter 306 includes a proximal flushing valve 307. The catheter 306 may be formed of polyurethane or of an elastomeric material such as silicone, for example, and the proximal flushing valve may include a longitudinal slit in the catheter shaft through to the infusion lumen thereof. The flushing valve 307 is normally closed, as shown in FIG. 3a. As shown in FIG. 3b, a syringe 308 fitted with an extension tube 309 may be used to flush (i.e., inject) pharmaceutical agent 310 into the catheter infusion lumen. This may be done by inserting the free end of the extension tube 309 into the flushing valve 307 and depressing the plunger of the syringe 308 to inject the pharmaceutical agent 310 contained within the syringe 308 into the infusion lumen of the catheter 306. The pharmaceutical agent 310 may be drawn from an ampoule 312 supplied with or separately from the pump system 300, as shown in FIGS. 3a and 3b. The level of pharmaceutical agent in the ampoule of FIG. 3b is shown to be lower than the level thereof in the ampoule of FIG. 3a, as the surgeon has drawn therefrom a volume of pharmaceutical agent 310 at least sufficient to fill the dead volume of the catheter 306. As shown in FIG. 3c, after the extension tube 309 is removed from the flushing valve 307, the valve elastically re-closes. The infusion lumen of the catheter 306 is now filled with the desired pharmaceutical agent 310 prior to implantation of the osmotic pump system 300 to eliminate or substantially reduce the time required in situ to fill the infusion lumen dead volume. The pharmaceutical agent 310 in the ampoule 312 may, but need not be, the same pharmaceutical agent as that loaded in the compartment 303. It is to be noted, moreover, that the method of reducing the time interval between implantation and delivery of a pharmaceutical agent illustrated in FIGS. 3a through 3c is not limited to osmotic-type pumps, but may readily be applied to any implantable pump that utilizes a catheter to deliver a pharmaceutical agent to a delivery site within a patient.

Preferably, the semipermeable membrane 305 of FIGS. 3a through 3c is pre-hydrated to further reduce the time between implantation and full operation of the pump system 300 at the intended infusion rate. This pre-hydration may be carried out as described relative to FIG. 1 or by including therewith the spacer and impermeable membrane structures described relative to FIGS. 2a through 2c. Similarly, the catheters 105 and 206 of FIGS. 1, 2a, 2b and 2c may be fitted with a flushing valve 307 to thereby enable the infusion lumen thereof to be at least partially filled with pharmaceutical agent 310 prior to implantation of the pump system 300. Other combinations of the kits, methods, systems, features and structures shown and described relative to FIGS. 1 through 3c are possible, and all such combinations are expressly within the scope of the present invention.

According to further embodiments of the present invention, the pump systems of FIGS. 1 through 3c may be pre-loaded with a pharmaceutical agent. For example, the osmotic pump systems 112, 200 and 300 described herein may be preloaded with one or more drugs for pain therapy, hormone therapy, gene therapy, angiogenic therapy, anti-tumor therapy, chemotherapy and/or other pharmaceutical therapy or therapies. In the case of pain therapy, for example, the pharmaceutical agent re-loaded into the pump systems described herein may include fentanyl, sufentanil and/or clonidine and mixtures thereof.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. A kit, comprising:
   a liquid tight container, enclosing:
      an implantable osmotic pump, the pump including a semipermeable membrane;
      a salt tablet, and
      an aqueous solution, wherein the aqueous solution is in fluid contact at least with the salt tablet and the semipermeable membrane, and wherein the salt tablet and the aqueous solution are enclosed by the liquid tight container and separate from the implantable osmotic pump, and maintain the semipermeable membrane in a hydrated state.

2. The kit of claim 1, further comprising a catheter attached to osmotic pump.

3. The kit of claim 2, wherein the catheter includes a flushing valve near a proximal end thereof.

4. The kit of claim 3, wherein the catheter is formed of an elastomer, polymeric or composite materials and wherein the flushing valve includes a longitudinal slit in the catheter.

5. The kit of claim 3, further including:
   an ampoule containing a pharmaceutical agent therein, and
   a syringe fitted with an extension tube, a distal end of which is dimensioned to fit within the proximal valve of the catheter.

6. The kit of claim 1, wherein the osmotic pump is preloaded with a pharmaceutical agent.

7. The kit of claim 6, wherein the osmotic pump is preloaded with at least one pharmaceutical agent for at least one therapy selected from a group including pain therapy, hormone therapy, gene therapy, angiogenic therapy, anti-tumor therapy, chemotherapy and other pharmaceutical therapy.

8. The kit of claim 6, wherein the pharmaceutical agent includes at least one of fentanyl, sufentanil, clonidine and mixtures thereof.

9. The kit of claim 1, wherein the catheter includes a distal valve mechanism adapted to prevent fluid back flow into the catheter.

10. The kit of claim 1, wherein the saturated saline solution is in fluid contact with the osmotic pump and the tablet.

11. The kit of claim 1, wherein the container includes a flexible fluid tight bag.

12. The kit of claim 1, wherein the bag includes at least one of polyethylene, PET, PETG and a gas permeable barrier film.

13. An implantable osmotic pump system, comprising:
   a pump housing having a proximal and a distal end, the pump housing including a pharmaceutical agent compartment and an osmotic agent compartment separated by a movable piston;
   a semipermeable membrane fitted to the proximal end;
   an impermeable membrane disposed over and away from the semipermeable membrane to define a fluid tight hydration compartment between the semipermeable membrane and the impermeable membrane, the impermeable membrane being configured to be breached prior to implantation of the osmotic pump system in a patient, and
   a saturated saline solution within the hydration compartment.

14. The pump system of claim 13, further comprising a salt tablet in the hydration compartment.

15. The pump system of claim 14, wherein the salt tablet includes NaCl.

16. The pump system of claim 13, wherein the pharmaceutical agent compartment is preloaded with a pharmaceutical agent.

17. The pump system of claim 16, wherein the pharmaceutical agent includes at least one of fentanyl, sufentanil and clonidine.

18. The pump system of claim 13, further including a catheter attached to the distal end of the pump housing and in fluid communication with the pharmaceutical agent compartment.

19. The pump system of claim 18, wherein the catheter includes an infusion lumen and an elastomeric proximal flushing valve.

20. The pump system of claim 18, wherein the catheter includes a distal valve mechanism adapted to prevent fluid back flow into the catheter.

21. The pump system of claim 13, wherein the impermeable barrier includes at least one of titanium, stainless steel platinum, platinum-iridium, polyethylene, PET and PETG.

22. The pump system of claim 13, wherein the osmotic pump system is preloaded with at least one pharmaceutical agent for at least one therapy selected from a group including pain therapy, hormone therapy, gene therapy, angiogenic therapy, anti-tumor therapy, chemotherapy and other pharmaceutical therapy.

23. A kit, comprising:
   an implantable osmotic pump system, comprising:
      a pump housing having a proximal and a distal end, the pump housing including a pharmaceutical agent compartment and an osmotic agent compartment separated by a movable piston; a semipermeable membrane fitted to the proximal end; an impermeable membrane disposed over and away from the semipermeable membrane to define a fluid tight hydration compartment between the semipermeable membrane and the impermeable membrane, the impermeable membrane being configured to be breached prior to implantation of the osmotic pump system in a patient and an aqueous solution within the hydration compartment, and a lancet adapted to breach the impermeable barrier.

24. The kit of claim 23, further including a catheter attached to the distal end of the pump housing and in fluid communication with the pharmaceutical agent compartment.

25. The kit of claim 24, wherein the catheter includes an infusion lumen and an elastomeric proximal flushing valve.

26. The kit of claim 25, further including a syringe adapted to inject pharmaceutical agent into the infusion lumen through the proximal valve.

27. The kit of claim 26, wherein the syringe includes an extension tube fitted thereto, the free end thereof being adapted to fit into the proximal flushing valve.

28. The kit of claim 26, further including an ampoule containing a sufficient volume of pharmaceutical agent to flush the infusion lumen prior to implantation of the osmotic pump system.

29. The kit of claim 23, wherein the pharmaceutical agent compartment is preloaded with a pharmaceutical agent.

30. The kit of claim 29, wherein the pharmaceutical agent includes at least one of fentanyl, sufentanil and clonidine.

31. The kit of claim 23, further including a salt tablet in the hydration compartment.

32. The kit of claim 23, wherein the impermeable barrier includes at least one of titanium and stainless steel.

33. The kit of claim 23, wherein the impermeable membrane is configured to be breached with a lancet prior to implantation of the osmotic pump system in a patient.

34. The kit of claim 23, wherein the osmotic pump system is preloaded with at least one pharmaceutical agent for at least one therapy selected from a group including pain therapy, hormone therapy, gene therapy, angiogenic therapy, anti-tumor therapy, chemotherapy and other pharmaceutical therapy.

35. The kit of claim 24, wherein the catheter includes a distal valve mechanism adapted to prevent fluid back flow into the catheter.

* * * * *